United States Patent
Galli et al.

(10) Patent No.: US 7,220,740 B2
(45) Date of Patent: May 22, 2007

(54) 1,4-DIAZABICYCLO[3.2.2]NONABENZOXAZOLE, -BENZOTHIAZOLE AND BENZIMIDAZOLE DERIVATIVES, PREPARATION AND THERAPEUTIC USE THEREOF

(75) Inventors: Frédéric Galli, Vaucresson (FR); Alistair Lochead, Charenton-le-Pont (FR); Axelle Samson, Charenton-le-Pont (FR)

(73) Assignee: Sanofi-aventis, Paris (FR)

(*) Notice: Subject to any disclaimer, the term of this patent is extended or adjusted under 35 U.S.C. 154(b) by 192 days.

(21) Appl. No.: 10/276,646

(22) PCT Filed: May 29, 2001

(86) PCT No.: PCT/FR01/01651

§ 371 (c)(1),
(2), (4) Date: Feb. 24, 2003

(87) PCT Pub. No.: WO01/92261

PCT Pub. Date: Dec. 6, 2001

(65) Prior Publication Data
US 2003/0153574 A1   Aug. 14, 2003

(30) Foreign Application Priority Data
May 31, 2000 (FR) .................... 00 06975

(51) Int. Cl.
*C07D 471/08* (2006.01)
*A61K 31/55* (2006.01)
*A61P 25/00* (2006.01)

(52) U.S. Cl. ..................... 514/221; 540/556
(58) Field of Classification Search ........... 540/556; 514/221
See application file for complete search history.

(56) References Cited

U.S. PATENT DOCUMENTS

| 5,478,939 | A | 12/1995 | Trybulski et al. ........ 544/336 |
| 6,407,095 | B1 | 6/2002 | Lochead et al. ........ 514/221 |
| 6,809,094 | B2 * | 10/2004 | O'Neill et al. ........ 514/221 |
| 2002/0086871 | A1 * | 7/2002 | O'Neill et al. ........ 514/260.1 |

FOREIGN PATENT DOCUMENTS

| EP | 0307140 | 3/1989 |
| WO | WO 00/34279 | 6/2000 |

* cited by examiner

*Primary Examiner*—Bruck Kifle
(74) *Attorney, Agent, or Firm*—Balaram Gupta

(57) ABSTRACT

Compound corresponding to the general formula (I)

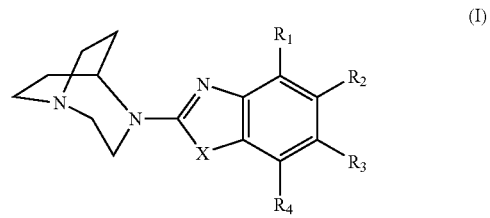

in which X represents an oxygen or sulphur atom or an NH group and $R_1$, $R_2$, $R_3$ and $R_4$ each represent a hydrogen or halogen atom or a nitro, amino, trifluoromethyl, trifluoroalkoxy, cyano, hydroxyl, $(C_1-C_6)$alkyl, $(C_1-C_6)$alkoxy or phenyl group.

Application in therapeutics.

4 Claims, No Drawings

1,4-DIAZABICYCLO[3.2.2]NONABENZOXAZOLE, -BENZOTHIAZOLE AND BENZIMIDAZOLE DERIVATIVES, PREPARATION AND THERAPEUTIC USE THEREOF

The compounds of the present invention correspond to the general formula (I)

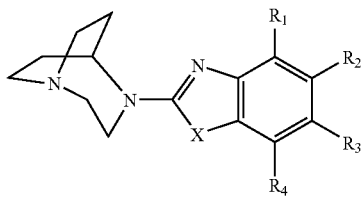

in which

X represents an oxygen or sulphur atom or an NH group and $R_1$, $R_2$, $R_3$ and $R_4$ each represent, independently of one another, a hydrogen or halogen atom or a nitro, amino, trifluoromethyl, trifluoroalkoxy, cyano, hydroxyl, $(C_1–C_6)$alkyl, $(C_1–C_6)$alkoxy or phenyl group.

The compounds of the invention can exist in the form of bases or of addition salts with acids.

In accordance with the invention, the compounds of general formula (I) can be prepared by reacting 1,4-diazabicyclo[3.2.2]nonane, of formula (II),

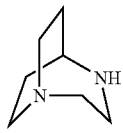

with a compound of general formula (III)

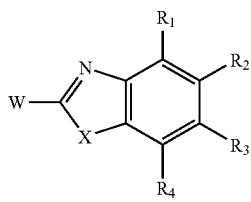

in which $R_1$, $R_2$, $R_3$ and $R_4$ are as defined above and W represents a halogen atom or a methylthio group, as described in *Ann. Chim.*, 1954, 44, 3.

The preparation of 1,4-diazabicyclo[3.2.2]nonane is described in *J. Med. Chem.*, 1993, 36, 2311–2320.

The compounds of general formula (III) are commercially available or are accessible by methods disclosed in the literature.

The examples which will follow illustrate the preparation of some compounds according to the invention. The elemental microanalyses and the IR and NMR spectra confirm the structures of the compounds obtained.

The numbers shown between brackets in the titles of the examples correspond to those in the 1st column in Table 1 given later.

In the names of the compounds, the hyphen "-" forms part of the word and the dash "_" is used only for the break at the end of the line; it is to be omitted in the absence of a break and should be replaced neither by a normal hyphen nor by a space.

EXAMPLE 1

Compound No. 1

4-(Benzoxazol-2-yl)-1,4-diazabicyclo[3.2.2]nonane Hydrobromide 1:2

0.126 g (1 mmol) of 1,4-diazabicyclo[3.2.2]nonane, 0.154 g (1 mmol) of 2-chlorobenzoxazole, 0.138 g (1 mmol) of potassium carbonate and 5 ml of pentan-1-ol are successively introduced into a 50 ml round-bottomed flask and the mixture is heated at 150° C. for 24 h.

It is filtered, the filtrate is concentrated under reduced pressure and the residue is purified by chromatography on a column of silica gel, elution being carried out with a 95/5/0.5 mixture of chloroform, methanol and aqueous ammonia.

0.054 g of product is obtained, which product is dissolved in 20 ml of isopropyl alcohol before adding a 33% solution of hydrobromic acid in acetic acid. The crystals obtained are collected by filtration. 0.057 g of product is obtained.

Melting point: 303–310° C.

EXAMPLE 2

Compound No. 2

4-(Benzothiazol-2-yl)-1,4-diazabicyclo[3.2.2]nonane Hydrobromide 1:2

0.17 g (1 mmol) of 2-chlorobenzothiazole, 0.126 g (1 mmol) of 1,-4-diazabicyclo[3.2.2]nonane and 0.138 g (1 mmol) of potassium carbonate in suspension in 5 ml of pentan-1-ol are successively introduced into a 50 ml round-bottomed flask and the mixture is heated at 155° C. for 24 h.

The inorganic products are separated by filtration, the solvent is evaporated under reduced pressure and the residue is purified by chromatography on a column of silica gel, elution being carried out with a 90/10/1 mixture of chloroform, ethanol and aqueous ammonia. The product obtained is dissolved in ethanol, a 33% solution of hydrobromic acid in acetic acid is added and the crystals obtained (0.063 g) are collected by filtration.

Melting point: 275–284° C.

EXAMPLE 3

Compound No. 6

4-(6-Chloro-7-nitrobenzothiazol-2-yl)-1,4-diazabicyclo[3.2.2]nonane 3.1. 2,6-Dichloro-7-nitrobenzothiazole.

4.76 g (23 mmol) of 2,6-dichlorobenzothiazole, in solution in 10 ml of concentrated sulphuric acid, are introduced into a 100 ml round-bottomed flask. The mixture is cooled to 17° C. in order to add a solution of 1.62 g (26 mmol) of nitric acid in 10 ml of sulphuric acid and then the temperature is allowed to rise to ambient temperature.

The reaction mixture is poured onto ice and a concentrated aqueous sodium-hydroxide solution is added to the aqueous phase to pH 10 and it is extracted with ethyl acetate. The combined organic phases are dried over sodium sulphate and are concentrated under reduced pressure.

The residue obtained is recrystallized from isopropyl ether. After filtration, 3.35 g of compound are isolated.

3.2. 4-(6-Chloro-7-nitrobenzothiazol-2-yl)-1,4-diazabicyclo[3.2.2]nonane.

1.29 g (5.15 mmol) of 2,6-dichloro-7-nitrobenzothiazole, 0.65 g (5.15 mmol) of 1,4-diazabicyclo[3.2.2]nonane, 0.71 g (5.15 mmol) of potassium carbonate and 60 ml of pentan-1-ol are successively introduced into a 250 ml round-bottomed flask. The mixture is heated at 150° C. for 14 h and is then cooled to ambient temperature before being filtered. The solvent is evaporated under reduced pressure and the residue is purified by chromatography on a column of silica gel, elution being carried out with a 98/2/0.2 mixture of chloroform, ethanol and aqueous ammonia. After recrystallizing from isopropyl alcohol, 0.54 g of crystals is collected by filtration.

M.p.: 157–160° C.

EXAMPLE 4

Compound No. 9

4-(6-Chloro-7-aminobenzothiazol-2-yl)-1,4-diazabicyclo[3.2.2]nonane 0.3 g (0.88 mmol) of 4-(6-chloro-7-nitrobenzothiazol-2-yl)-1,4-diazabicyclo[3.2.2]nonane, in solution in 2.8 ml of water and 1.4 ml of acetic acid, is introduced into a 25 ml round-bottomed flask. 2.9 g (2.57 mmol) of iron powder are subsequently added and the mixture is heated at 45–50° C. for 1.5 h.

It is cooled to 4° C. and 3.6 ml of a concentrated aqueous sodium hydroxide solution are added.

The reaction mixture is filtered, the solvents are evaporated under reduced pressure and the residue is purified by chromatography on a column of silica gel, elution being carried out with a 97/3/0.3 mixture of chloroform, ethanol and aqueous ammonia. After recrystallizing from ethyl ether, 0.14 g of crystals is collected by filtration.

Melting point: 189–194° C.

EXAMPLE 5

Compound No. 10

4-(4-Methylbenzoxazol-2-yl)-1,4-diazabicyclo[3.2.2]nonane Hydrochloride 1:2

5.1. 2-Mercapto-4-methylbenzoxazole.

5 g (41 mmol) of 2-amino-3-methylphenol and 6.51 g (41 mmol) of potassium O-ethyl dithiocarbonate, in suspension in 70 ml of ethanol, are successively introduced into a 500 ml round-bottomed flask and the mixture is heated at reflux for 24 h. The solvent is removed by evaporation under reduced pressure, the residue is taken up in 50 ml of water and 4 ml of acetic acid are added. The precipitate obtained is filtered off, rinsed with water and dried under vacuum.

3.97 g of product are obtained in the form of a solid.

M.p.: 191–195° C.

5.2. 2-Methylthio-4-methylbenzoxazole.

3.97 g (24 mmol) of 2-mercapto-4-methylbenzoxazole in solution in 40 ml of water and 3.2 ml of a 30% aqueous sodium hydroxide solution are introduced into a 250 ml round-bottomed flask and the mixture is heated at reflux for 2 h.

It is cooled to ambient temperature, 2.27 ml (24 mol) of dimethyl sulphate are added and the mixture is stirred at room temperature for 20 h.

The aqueous phase is extracted with ethyl acetate and the organic phases are dried over sodium sulphate and are concentrated under reduced pressure.

3.61 g of product are obtained in the form of an oil.

5.3. 4-(4-Methylbenzoxazol-2-yl)-1,4-diazabicyclo[3.2.2]nonane Hydrochloride 1:2.

0.7 g (5.55 mmol) of 1,4-diazabicyclo[3.2.2]nonane and 0.9 g (5 mmol) of 2-methylthio-4-methylbenzoxazole are introduced into a 100 ml round-bottomed flask and the mixture is heated at 130° C. for 8 h.

The residue is purified by chromatography on a column of silica gel, elution being carried out with a 97/3/0.3 mixture of chloroform, ethanol and aqueous ammonia.

0.46 g of an oil is obtained, which oil is dissolved in 15 ml of ethanol in order to add 0.7 ml of a 5N solution of hydrochloric acid in isopropyl alcohol. The crystals formed are subsequently collected by filtration and dried under vacuum. 0.25 g of hydrochloride is obtained.

Melting point: 294–303° C.

EXAMPLE 6

Compound No. 7

4-(5-Aminobenzoxazol-2-yl)-1,4-diazabicyclo[3.2.2]nonane 0.403 g (1.4 mmol) of 4-(5-nitrobenzoxazol-2-yl)-1,4-diazabicyclo[3.2.2]nonane, obtained in the way described in the preceding examples, in solution in 4.5 ml of water and 2.2 ml of acetic acid, is introduced into a 25 ml round-bottomed flask. 0.226 g (4.05 mmol) of iron powder is subsequently added and the mixture is heated at 45–50° C. for 1 h.

After cooling to ambient temperature, 5 ml of a concentrated aqueous sodium hydroxide solution are added and the mixture is filtered, the filtrate is concentrated under reduced pressure and the residue is purified by chromatography on a column of silica gel, elution being carried out with a 97/3/0.3 mixture of chloroform, ethanol and aqueous ammonia.

The product obtained (0.17 g) is recrystallized from ethyl ether and the crystals are collected by filtration.

Melting point: 161–164° C.

The chemical structures and the physical properties of a few compounds of the invention are illustrated in the following table.

TABLE (I)

| No. | X | $R_1$ | $R_2$ | $R_3$ | $R_4$ | Salt | M.p. (°) |
|---|---|---|---|---|---|---|---|
| 1 | O | H | H | H | H | HBr 2:1 | 303–310 |
| 2 | S | H | H | H | H | HBr 2:1 | 275–284 |
| 3 | NH | H | H | H | H | HBr 1:1 | 271–285 |
| 4 | O | H | $NO_2$ | H | H | — | 158–160 |
| 5 | S | H | H | $NO_2$ | H | — | 173–175 |
| 6 | S | H | H | Cl | $NO_2$ | — | 157–160 |
| 7 | O | H | $NH_2$ | H | H | — | 161–164 |
| 8 | S | H | H | $NH_2$ | H | — | 176–182 |
| 9 | S | H | H | Cl | $NH_2$ | — | 189–194 |
| 10 | O | $CH_3$ | H | H | H | HCl 2:1 | 294–303 |
| 11 | O | H | $CH_3$ | H | H | HCl 2:1 | 298–307 |
| 12 | O | H | $OCH_3$ | H | H | HBr 2:1 | 269–271 |
| 13 | O | H | $C_6H_5$ | H | H | HBr 2:1 | 299–306 |
| 14 | O | H | Cl | H | H | HBr 2:1 | 301–304 |

Key

In the "Salt" column, "-" denotes a compound in the form of the base, "HBr" denotes a hydrobromide and "HCl" denotes a hydrochloride. The acid:base molar ratio is shown opposite.

The compounds of the invention have formed the subject of tests which have demonstrated their advantage as therapeutic substances.

Thus, they have been studied with regard to their affinity with respect to nicotinic receptors comprising the $\alpha_7$ subunit according to the methods described by Marks and Collins in *Mol. Pharmacol.*, 1982, 22, 554, and by Marks et al. in *Mol. Pharmacol.*, 1986, 30, 427.

Male OFA rats weighing 150 to 200 g are decapitated and the entire brain is quickly removed, homogenized using a Polytron™ mill in 15 volumes of a 0.32M sucrose solution at 4° C. and then centrifuged at 1 000 g for 10 min. The pellet is removed and the supernatant is centrifuged at 8 000 g for 20 min at 4° C. The pellet is recovered and is homogenized using a Polytron™ mill in 15 volumes of doubly-distilled water at 4° C. and is then centrifuged at 8 000 g for 20 min. The pellet is removed and the supernatant and the layer of skin (buffy coat) are centrifuged at 40 000 g for 20 min. The pellet is recovered, is resuspended with 15 volumes of doubly-distilled water at 4° C. and is centrifuged a further time at 40 000 g for 20 min before being stored at −80° C.

On the day of the experiment, the tissue is slowly defrosted and is suspended in 5 volumes of buffer. 150 µl of this membrane suspension are preincubated at 37° C. for 30 min in darkness in the presence or in the absence of the test compound. The membranes are then incubated for 60 min at 37° C. in darkness in the presence of 50 µl of 1 nM [$^3$H]α-bungarotoxin in a final volume of 250 µl of HEPES 20 mM buffer. The reaction is halted by filtration through Whatman GF/C™ filters pretreated for 3 h with 0.05% polyethylenimine. The filters are rinsed with two times 5 ml of buffer at 4° C. and the radioactivity retained on each filter is measured by liquid scintigraphy. The nonspecific binding in the presence of 1 µM α-bungarotoxin is determined; the nonspecific binding represents approximately 60% of the total binding recovered on the filter. The percentage of inhibition of the specific binding of [$^3$H]α-bungarotoxin is determined for each concentration of studied compound and then the $IC_{50}$ value, the concentration of compound which inhibits 50% of the specific binding, is calculated.

The $IC_{50}$ values of the acutest compounds of the invention lie between 0.021 and 0.125 µM.

The compounds of the present invention were also studied with regard to their affinity with respect to nicotinic receptors comprising the $\alpha_4\beta_2$ subunit according to the methods described by Anderson and Arneric in *Eur. J. Pharmacol.*, 1994, 253, 261, and by Hall et al. in *Brain Res.*, 1993, 600, 127.

Male Sprague-Dawley rats weighing 150 to 200 g are decapitated and the entire brain is quickly removed, homogenized in 15 volumes of a 0.32M sucrose solution at 4° C. and then centrifuged at 1 000 g for 10 min. The pellet is removed and the supernatant is centrifuged at 20 000 g for 20 min at 4° C. The pellet is recovered and is homogenized using a Polytron™ mill in 15 volumes of doubly-distilled water at 4° C. and is then centrifuged at 8 000 g for 20 min. The pellet is removed and the supernatant and the layer of skin (buffy coat) are centrifuged at 40 000 g for 20 min. The pellet is recovered, is resuspended in 15 ml of doubly-distilled water and is centrifuged a further time at 40 000 g before being stored at −80° C.

On the day of the experiment, the tissue is slowly defrosted and is suspended in 3 volumes of buffer. 150 µl of this membrane suspension are incubated at 4° C. for 120 min in the presence of 100 µl of 1 nM [$^3$H]-cytisine in a final volume of 500 µl of buffer, in the presence or in the absence of test compound. The reaction is halted by filtration through Whatman GF/B™ filters pretreated with polyethylenimine. The filters are rinsed with two times 5 ml of buffer at 4° C. and the radioactivity retained on the filter is measured by liquid scintigraphy. The nonspecific binding in the presence of 10 µM (−)-nicotine is determined; the nonspecific binding represents 75 to 85% of the total binding recovered on the filter. The percentage of inhibition of the specific binding of [$^3$H]-cytisine is determined for each concentration of studied compound and then the $IC_{50}$ value, the concentration of compound which inhibits 50% of the specific binding, is calculated.

The $IC_{50}$ values of the acutest compounds of the invention lie between 2 and 10 µM.

The preceding results show that the compounds of the invention are selective ligands for $\alpha_7$ subunits with respect to the $\alpha_4\beta_2$ subunits of the nicotinic receptor.

The results of the various tests suggest the use of the compounds in the treatment or prevention of disorders related to a dysfunctioning of the nicotinic receptors, in particular in the central nervous system.

These disorders comprise detrimental cognitive changes, more specifically detrimental memory changes, but also detrimental attentional changes, related to Alzheimer's disease, to pathological ageing (Age Associated Memory Impairment, AAMI), to Parkinsonian syndrome, to trisomy 21 (Down's syndrome), to Korsakoff's alcoholic syndrome or to vascular dementias (multiinfarct dementia, MID).

The compounds—of the invention might also be of use in the treatment of motor disorders observed in Parkinson's disease or other neurological diseases, such as Huntington's chorea, Tourette's syndrome, tardive dyskinesia and hyperkinesia.

The compounds of the invention can also constitute a curative or symptomatic treatment of strokes and cerebral hypoxic episodes. They can be used in the case of psychiatric pathologies: schizophrenia, depression, anxiety, panic attacks or obsessive-compulsive behaviour.

They can prevent symptoms due to weaning from tobacco, from alcohol and from various dependence-inducing substances, such as cocaine, LSD, cannabis or benzodiazepines.

This is why another subject-matter of the present invention is pharmaceutical compositions comprising an effective dose of at least one compound according to the invention, in the form of the base or a pharmaceutically acceptable salt or solvate, as a mixture, if appropriate, with suitable excipients.

The said excipients are chosen according to the pharmaceutical form and the method of administration desired.

The pharmaceutical compositions according to the invention may thus be intended for oral, sublingual, subcutaneous, intramuscular, intravenous, topical, intratracheal, intranasal, transdermal, rectal or intraocular administration.

The unit administration forms can be, for example, tablets, gelatin capsules, granules, powders, solutions or suspensions to be taken orally or to be injected, transdermal patches or suppositories. Ointments, lotions and collyria can be envisaged for topical administration.

The said unit forms are dosed to allow a daily administration of 0.01 to 20 mg of active principle per kg of body weight, according to the pharmaceutical dosage form.

To prepare tablets, a pharmaceutical vehicle, which can be composed of diluents, such as, for example, lactose, microcrystalline cellulose or starch, and formulation adjuvants, such as binders (polyvinylpyrrolidone, hydroxypropylmethylcellulose, and the like), flow agents, such as silica, or lubricants, such as magnesium stearate, stearic acid, glyceryl tribehenate or sodium stearylfumarate, is added to the micronized or unmicronized active principle. Wetting or surface-active agents, such as sodium lauryl sulphate, can also be added.

The preparation techniques can be direct tableting, dry granulation, wet granulation or hot melt.

The tablets can be bare, coated with sugar, for example with sucrose, or coated with various polymers or other appropriate materials. They can be designed to make possible rapid, delayed or sustained release of the active principle by virtue of polymer matrices or of specific polymers used in the coating.

To prepare gelatin capsules, the active principle is mixed with dry pharmaceutical vehicles (simple mixing, dry or wet granulation, or hot melt) or liquid or semisolid pharmaceutical vehicles.

The gelatin capsules can be hard or soft and coated or uncoated with a thin film, so as to have a rapid, sustained or delayed activity (for example, for an enteric form).

A composition in the form of a syrup or an elixir or for administration in the form of drops can comprise the active principle in conjunction with a sweetener, preferably a calorie-free sweetener, methylparaben or propylparaben, as antiseptic, a flavour enhancer and a colorant.

The water-dispersible powders and granules can comprise the active principle as a mixture with dispersing agents or wetting agents, or dispersing agents, such as polyvinylpyrrolidone, as well as with sweeteners and flavour-correcting agents.

Recourse is had, for rectal administration, to suppositories prepared with binders which melt at the rectal temperature, for example cocoa butter or polyethylene glycols.

Use is made, for parental administration, of aqueous suspensions, isotonic saline solutions or injectable sterile solutions comprising pharmacologically compatible dispersing agents and/or wetting agents, for example propylene glycol or butylene glycol.

The active principle can also be formulated in the form of microcapsules, optionally with one or more vehicles or additives or else with a polymer matrix or with a cyclodextrin (transdermal patches or sustained release forms).

The topical compositions according to the invention comprise a medium compatible with the skin. They can be provided in particular in the form of aqueous, alcoholic or aqueous/alcoholic solutions, of gels, of water-in-oil or oil-in-water emulsions having the appearance of a cream or of a gel, of microemulsions or of aerosols or in the form of vesicular dispersions comprising ionic and/or nonionic lipids. These pharmaceutical dosage forms are prepared according to methods conventional in the fields under consideration.

Finally, the pharmaceutical compositions according to the invention can comprise, in addition to a compound of the general formula (I), other active principles which can be of use in the treatment of the disorders and diseases indicated above.

The invention claimed is:

1. A compound of formula (I)

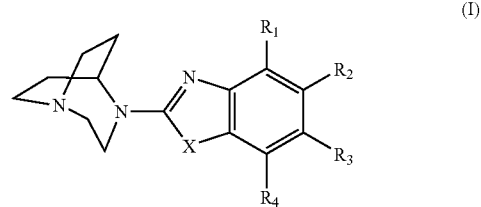

in which
X represents an oxygen or sulphur atom or an NH group and $R_1$, $R_2$, $R_3$ and $R_4$ each represent, independently of one another, a hydrogen or halogen atom or a nitro, amino, trifluoromethyl, trifluoroalkoxy, cyano, hydroxyl, $(C_1–C_6)$ alkyl, $(C_1–C_6)$alkoxy or phenyl group, or a pharmaceutically acceptable salt thereof.

2. A process for the preparation of a compound according to claim 1 wherein 1,4-diazabicyclo[3.2.2]nonane is reacted with a compound formula (III)

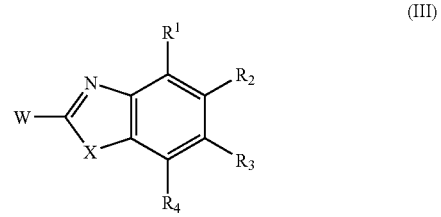

in which $R_1$, $R_2$, $R_3$ and $R_4$ are as defined in claim 1 and W represents a halogen atom or a methylthio group.

3. A method for the treatment or prevention of symptoms due to weaning from tobacco, which comprises administering to a patient in need of such treatment an effective amount of a compound according to claim 1.

4. A pharmaceutical composition comprising an effective amount of a compound according to claim 1, in combination with an excipient.

* * * * *